US005643569A

United States Patent [19]
Jain et al.

[11] Patent Number: 5,643,569
[45] Date of Patent: Jul. 1, 1997

[54] PREPARATION OF AGAROSE COATED, SOLID AGAROSE-COLLAGEN BEADS CONTAINING SECRETORY CELLS

[75] Inventors: Kanti Jain, New York, N.Y.; Albert L. Rubin, Englewood, N.J.; Barry H. Smith, New York, N.Y.

[73] Assignee: The Rogosin Institute, New York, N.Y.

[21] Appl. No.: 483,728

[22] Filed: Jun. 7, 1995

Related U.S. Application Data

[63] Continuation of Ser. No. 181,269, Jan. 13, 1994, abandoned.

[51] Int. Cl.$^6$ .......................... A61K 35/12; C12N 11/02; C12N 11/10; C12N 5/00
[52] U.S. Cl. .......................... 424/93.7; 435/177; 435/178; 435/182; 435/382; 435/366
[58] Field of Search .......................... 435/174, 177, 435/178, 182; 424/93.7

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,409,331 | 10/1983 | Lim | 435/178 |
| 4,647,536 | 3/1987 | Mosbach et al. | 435/177 |
| 4,663,286 | 5/1987 | Tsang et al. | 435/178 |
| 4,673,566 | 6/1987 | Goosen et al. | 424/19 |
| 4,798,786 | 1/1989 | Tice et al. | 435/177 |
| 4,902,295 | 2/1990 | Walthall et al. | 623/11 |
| 4,971,833 | 11/1990 | Larsson et al. | 427/213.33 |
| 4,997,443 | 3/1991 | Walthall et al. | 623/11 |
| 5,053,332 | 10/1991 | Cook et al. | 435/178 |
| 5,227,298 | 7/1993 | Weber et al. | 435/178 |

OTHER PUBLICATIONS

Brodelius, et al., "Entrapment of Plant Cells In Different Matrices," FEBS Letters: 122(2): 312–316 (1980) was cited by the examiner in the parent application.

Iwata, et al., Journal of Biomedical Materials Research, vol. 26, 1992, pp. 967–977.

*Primary Examiner*—David M. Naff
*Attorney, Agent, or Firm*—Felfe & Lynch

[57] ABSTRACT

Biological agents such as secretory cells are encapsulated in a hydrophilic gel made of agarose or collagen-agarose and gelatin sponge-agarose combinations. In a preferred embodiment, semi-solid beads are formed from a suspension containing collagen, agarose and secretory cells such as pancreatic islets, the collagen is polymerized to form solid, agarose-collagen beads and the solid beads are coated with agarose. Coating is preferably by rolling the solid beads in about 5–10% agarose, contacting the rolled beads with mineral oil and washing oil from the beads. Beads containing secretory cells can be transplanted into a mammal to treat a condition caused by impaired secretory cell function.

17 Claims, 8 Drawing Sheets

PREPARATION OF AGAROSE COATED, SOLID AGAROSE-COLLAGEN BEADS CONTAINING SECRETORY CELLS

This application is a continuation of application Ser. No. 08/181,269 filed Jan. 13, 1994, now abandoned.

FIELD OF THE INVENTION

The present invention relates to macroencapsulation of secretory cells in a hydrophilic gel material, therapeutic methods employing the macroencapsulated secretory cells, and preserving the secretory cells by macroencapsulation.

BACKGROUND OF THE INVENTION

Secretory cells are cells that are characterized by secreting biological products, such as, but not limited to, hormones (e.g., insulin), growth factors, cytokines, and so forth. Their role in biological processes is well known, and need not be set forth here. A number of diseases and pathological conditions are related to a failure of the secretory cells to work properly, such as a deficient production of the secretory products, e.g. hypothyroidism and cretin dwarfism, both due to thyroid hormone deficiency, hypophysial dwarfism due to pituitary growth hormone deficiency, Lesch-Hyhan Syndrome due to hypoxanthine-guanine phosphoribosyltransferase deficiency, fulminant hepatic failure due to the hepatotrophic factor deficiency, extracellular matrix disease due to chondrocyte deficiency, and insulin dependant diabetes due to insulin deficiency.

One approach to treat such conditions is to transplant the secretory cells into the patient. The transplanted material, in order to be clinically safe and effective, must (1) be non-immunogenic, non-thrombogenic, bio-stable, and completely non-toxic to cells and tissues of the host, (2) maintain cell viability for an extended period of time, (3) permit free passage of nutrients, secretagogues (a substance that stimulates secretion), and cell products, (4) facilitate surgical implantation and cell reseeding, and (5) be easily fixed in place and, likewise, removed.

Pancreatic islet tansplantation to treat insulin-dependant diabetes has been the subject of renewed interest due to technological advances in isolating islets of Langerhans. By way of background, the human pancreas contains islets of Langerhans (hereinafter "pancreatic islets") that are scattered throughout the exocrine pancreas with some concentrations near the pancreatic ducts. The pancreatic islets, taken together, can be thought of as a single endocrine organ occupying around 1% of the volume of the pancreas. Within the pancreas, small islets (up to 160 µm diameter) tend to distribute throughout the exocrine tissue. These small islets represent 75% of the islets in number but only about 15% in volume. Islets greater than 250 µm diameter constitute only 15% of the total number of islets but 60% of the volume. These islets are localized near larger ducts and blood vessels, and are not surrounded by acinar tissue. A human pancreas may contain over 1 million islets, and each islet typically consists of several thousand cells. Each islet is comprised of a central core of insulin producing beta cells (B-cells) and a surrounding mantle of glucagon containing alpha cells (A-cells), somatostatin secreting delta cells (D-cells) and pancreatic polypeptide containing cells (PP-cells). Insulin producing B-cells makeup the majority of the cells, and comprise up to about 80% of the islets in a human.

The clinical applications of pancreatic islet transplantation have been limited by the inability to prevent islet allograft-xenograft rejection, i.e., a rejection of the transplanted pancreatic islets due to the host's immune system attacking the transplanted pancreatic islets. To counteract the rejection, the pancreatic islets have been transplanted in combination with the administration of immunosuppressive agents.

Immunosuppressive therapy, however, has proved to be a double-edged sword; while reducing the risk of rejection, it impairs the body's overall immunological defenses. Various methods of protecting the transplanted tissue from the host immune response have been explored by many investigators. As discussed below, although temporary success has been reported (See hey, Diabetes Reviews 1 (1):76 (1993), effective long-term methods have yet to be achieved.

The five major approaches to protecting the transplanted tissue from the host's immune response all involve attempts to isolate the transplanted tissue from the host's immune system. The immunoisolation techniques used to date include: extravascular diffusion chambers, intravascular diffusion chambers, intravascular ultrafiltration chambers, microencapsulation, and macroencapsulation. All of these methods have failed, however, due to one or more of the following problems; a host fibrotic response to the implant material, instability of the implant material, limited nutrient diffusion across semi-permeable membranes, secretagogue and product permeability, and diffusion lag-time across semi-permeable membrane barriers.

For example, a microencapsulation procedure for enclosing viable cells, tissues, and other labile biological membranes within a semipermeable membrane was developed by Lira in 1978. (Lim, Research report to Damon Corporation (1978)). Lim used microcapsules of alginate and poly L-lysine to encapsulate the islets of Langerhans. In 1980, the first successful in vivo application of this novel technique in diabetes research was reported ((Lim, et al., Science 210:908 (1980)). The implantation of these microencapsulated islets of Langerhans resulted in sustaining a euglycemic state in diabetic animals. Other investigators, however, repeating these experiments, found the alginate to cause a tissue reaction and were unable to reproduce Lira et al's results (Lamberti, et al., Applied Biochemistry and Biotechnology 10:101 (1984); Dupuy, et al., Jour. Biomed. Material and Res. 22:1061 (1988); Weber, et al., Transplantation 49:396 (1990); and Soon-Shiong, et al., Transplantation Proceedings 22:754 (1990)). The water solubility of these polymers is now considered to be responsible for the limited stability and biocompatibility of these microcapsules in vivo ((Dupuy, et al. supra, Weber, et al. supra, Soon-Shiong, et al., supra, and Smidsrod, Faraday Discussion of Chemical Society 57:263 (1974)).

Recently, Iwata et al., (Iwata, et al. Jour. Biomedical Material and Res. 26:967 (1992)) utilized agarose for microencapsulation of allogeneic pancreatic islets and discovered that it could be used as a medium for the preparation of microbeads. In their study, 1500–2000 islets were microencapsulated individually in 5% agarose and implanted into streptozotocin-induced diabetic mice. The graft survived for a long period of time, and the recipients maintained normoglycemia indefinitely.

Their method, however, suffers from a number of drawbacks. It is cumbersome and inaccurate. For example, many beads remain partially coated and several hundred beads of empty agarose form. Additional time is thus required to separate encapsulated islets from empty beads. Moreover, most of the implanted microbeads gather in the pelvic cavity, and a large number of islets are required in completely coated individual beads to achieve normoglycemia.

Furthermore, the transplanted beads are difficult to retrieve, tend to be fragile, and will easily release islets upon slight damage.

A macroencapsulation procedure has also been tested. Macrocapsules of various different materials, such as poly-2-hydroxyethyl-methacrylate, poly vinylchloride-co-acrylic acid, and cellulose acetate were made for the immunoisolation of islets of Langerhans. (See Altman, et al., Diabetes 35:625 (1986); Altman, et al., Transplantation American Society of Artificial Internal Organs 30:382 (1984); Ronel, et al., Jour. Biomedical Material Research 17:855 (1983); Klomp, et al., Jour. Biomedical Material Research 17:865–871 (1983)). In all these studies, only a transitory normalization of glycemia was achieved.

Archer et al., Journal of Surgical Research, 28:77 (1980), used acrylic copolymer hollow fiber to temporarily prevent rejection of islet xenografts. They reported long-term survival of dispersed neonatal murine pancreatic grafts in hollow fibers which were transplanted into diabetic hamsters. Recently hey et al., Science 254:1782–1784 (1991) confirmed their results, but found the euglycemic state to be a transient phase. They found that when the islets are injected into the fiber, they aggregate within the hollow tube and result in necrosis in the central portion of the islet masses. The central necrosis precluded prolongation of the graft. To solve this problem, they used alginate to disperse the islets in the fiber. Using this method they were able to achieve long-ten graft survival. However, this experiment .has not been extensively repeated. Therefore, the membrane's function as an islet transplantation medium in humans is questionable.

Thus, there exists a need for achieving secretory cell transplantation, and in particular, pancreatic islet allograft and xenograft survival without the use of chronic immunosuppressive agents.

The inventors have surprisingly discovered that macroencapsulating secretory cells in a hydrophilic gel material results in a functional, non-immunogenic, macrobead that can be transplanted into animals and can be stored for long lengths of time. The macroencapsulation of the secretory cells of the present invention provides a more effective and manageable technique for secretory cell transplantation. The macroencapulation technique can also be used to macroencapsulate other biological agents, such as enzymes, microorganisms, trophic agents including recombinantly produced trophic agents, cytotoxic agents, and chemotherapeutic agents. The macroencapsulated biological agents can be administered to treat conditions known to respond to the biological agent.

SUMMARY OF THE INVENTION

It is therefore an object of the present invention to provide a secretory cell macrobead that can be transplanted into animals to treat conditions caused by an impaired functioning of the host's secretory cells.

It is a further object of this invention to provide a secretory cell macrobead that can be stored for long lengths of time.

In accomplishing these and other objects, there has been provided, in accordance with one aspect of the present invention a method of producing an agarose coated, agarose-collagen secretory cell macrobead; an agarose coated, gelfoam secretory cell macrobead; and a agarose coated, agarose secretory cell macrobead.

In another aspect of the invention, there is provided a method of treating a patient having a condition characterized by an insufficiency in a secretory cell product, comprising transplanting into said patient a therapeutically affective amount of secretory cell macrobeads selected from the group consisting of agarose coated, agarose-collagen secretory cell macrobeads; agarose coated, gelfoam secretory cell macrobeads; and agarose coated, agarose secretory cell macrobeads.

In yet a further aspect of the invention, there is provided a method for preserving secretory cells, comprising forming macrobeads selected from the group consisting of agarose coated, agarose-collagen secretory cell macrobeads; agarose coated, gelfoam secretory cell macrobeads; and agarose coated, agarose secretory cell macrobeads; and incubating said secretory cell macrobeads.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to macroencapsulation of biological agents, and preferably, secretory cells in a hydrophilic gel material, therapeutic methods employing the macroencapsulated biological agents, and preferably, secretory cells, and preserving the biological agents, preferably secretory cells by macroencapsulation. The hydrophilic gel material comprises agarose, and combinations of collagen-agarose and gelatin sponge-agarose. Gelatin sponge will hereinafter be referred to as gelfoam.

The term biological agent denotes a living organism and its products, e.g. proteins, enzymes, hormones, polypeptides, serum, antibodies, and antibiotics and also genetically engineered cells. Biological agents include enzymes, e.g., glucose oxidase, lactase complex, microorganisms, e.g., *Klebsiella aerogenes* for removal of ammonia and urea, trophic agents, including recombinantly produced trophic agents, e.g, recombinantly produced growth hormone, and cytotoxic agents.

The term secretory cell includes a pancreatic islet, although technically, a pancreatic islet is not a secretory cell, but mostly a cluster of secretory cells scattered throughout the pancreas and comprising its endocrine potion. In humans, they are composed of at least four different types of secretory cells: alpha cells which secrete the hyperglycemic factor, glucagon; beta cells which are the most abundant (70%-80%) and secrete insulin; delta cells which secrete somatostatin, and polypeptide cells which secrete polypeptide hormone.

As explained previously, transplanted material must be compatible with the host. Agarose has a long history of use in biological research, and its quality is well-controlled. Collagen is the most abundant protein in mammals, provides firm mechanical support and serves as the biological space for cell replication, differentiation, organogenesis, individual growth and wound repair. Collagen also has good biocompatibility. Gelfoam is non-immunogenic and has been used extensively in surgical procedures. It is also well-tolerated by secretory cells.

The biological agents, and preferably, secretory cells, are first isolated using procedures well known in the art. In a preferred embodiment, pancreatic islets are cultured at either 4° C., 24° C., or at 37° C. before they are macroencapsulated. This method allows one to select only surviving islets after the isolation trauma. Also, the islets become less immunogenic resulting in the protection of macrobeads form fibrosis.

In one embodiment of the invention, a biological agent, preferably pancreatic islets, and more preferably about 50,000–700,000 pancreatic islets, are suspended in an aqueous solution of collagen, preferably about 0.5%-2% atellocollagen solution. Atellocollagen is obtained by treating collagen with pepsin, which removes antigenic telopeptides, responsible for intermolecular cross linkage of collagen. About 0.5%-5% of agarose, preferably about 1%, is then added to the suspended pancreatic islets to form pancreatic islets suspended in a mixture of collagen and agarose. The mixture containing the pancreatic islets is then transformed into a semisolid bead using techniques well known in the art, preferably by dropping the mixture onto mineral oil or a Teflon® sheet. The semisolid bead is then transferred to an antibiotic medium, washed, and then incubated under standard conditions to polymerize the collagen, preferably at 37° C. in a humidified 5% $CO_2$ atmosphere, whereby a solid collagen-agarose macrobead is formed.

In another embodiment of the invention, a biological agent, preferably pancreatic islets, and more preferably about 50,000–700,000 pancreatic islets, are spread onto the surface (3-5 cm) of a gelatin sponge. The gelatin sponge is then rolled into a sphere. Agarose, 3%-5%, is poured onto the sphere to form a bead.

In yet another embodiment of the invention, a biological agents, preferably pancreatic islets, and more preferably about 50,000–700,000 pancreatic islets, are placed in an agarose solution ranging from about 0.5%-5% agarose, preferably about 1% agarose. The mixture is then transformed into a macrobead by contacting the mixture to mineral oil or teflon. The bead is then transferred to an antibiotic medium, washed, and incubated overnight, preferably at 37° C. in a humidified 5% $CO_2$ atmosphere.

In all the aforementioned embodiments, the macrobeads are uniformly coated with agarose, preferably by rolling the bead 3-4 times in a Teflon spoon containing about 500-2,000 µl of 5%-10% agarose Similarly, the term biological agent macrobeads, as used herein, denotes macroencapsulated biological agents in the form of a bead.

The macrobeads may be used as a vehicle to deliver the biological agent to the body where the agent will perform its known function. More than one type of biological agent may be encapsulated in one bead. For example, a macrobead can contain multiple enzymes, such as hemoglobin and glucose oxidase. Such a bead can be administered to remove bilirubin. These beads can be used either for oral administration of digestive enzymes (lactase complex) or for selective removal of undesirable amino acids from the body. Encapsulation of the enzymes will also prevent the degradation of the enzyme in the tureen. Furthermore, recombinant gene products can be safely delivered using encapsulation as the medium. *K. aerogenes* gene, for example, can be macroencapsulated in macrobeads for urea and ammonia removal. Where the biological agent is immunogenic to the host, the macrobead allows the administration of the biological agent without the use of immunosuppressant or with decreased amounts of immunosuppressant.

The secretory macrobeads may be used to treat conditions caused by an impaired functioning of the secretory cells of the subject, e.g. insulin dependant diabetes, growth factor deficiency disorder, and hormonal disorders, by transplanting the secretory cell macrobeads into the subject. The macrobeads may be inserted into the appropriate location for that particular treatment. For example, macrobeads containing hepatocytes can be implanted into the abdominal cavity to treat diseases related to liver non-function. A preferred application is transplanting 5–10 pancreatic islet macrobeads, each containing 50,000–700,000 pancreatic islets, into a patient to treat insulin-dependant diabetes. The macrobeads can be inserted into the peritoneal cavity.

The secretory cell macrobeads are transplanted into a patient in an amount sufficient to treat the condition. An mount adequate to accomplish this is defined as a "therapeutically effective mount" or "efficacious amount". Amounts effective for this use will depend upon the severity of the condition, the general state of the patient, the route of administration, the placement of macrobeads, and whether the secretory cell macrobeads are being administered in combination with other drugs.

The secretory macrobeads can be used for allogeneic and xenogeneic transplantation in combination with immunosuppressants or preferably, without immunosuppressants. In a preferred embodiment, patients having chronic or acute insulin dependant diabetes are treated by xenotransplantating animal pancreatic islets, e.g. porcine, bovine, murine, rat, picin, or any other suitable species into the patient without the use of immunosuppressants. The secretory cell macrobeads can also be administered in combination with other therapeutic agents, e.g. the commonly used triple drug therapy (cyclosporine, azathioprine, and hydrocortisone), rapamycin, deoxyspergualin or antibodies, to treat the condition.

The macrobeads can also be used as a means to store the biological agents, and preferably secretory cells, for extended periods of time. To maintain the viability of the biological agents, and preferably secretory cells, the biological agents, and preferably secretory cell macrobeads are incubated until they are transplanted in the animal.

When the secretory cells are pancreatic islets, the pancreatic islet macrobeads are incubated at a temperature of 24° C. or 37° C.

EXAMPLES

Example I
Pancreatic Islet Isolation

Pancreatic islets were isolated from rats by a modification of the method disclosed in Gotbh et al., Transplantation 40:437 (1985).

Collagenase solution (collagenase Type XI, Sigma Chemical, St. Louis, Mo.; 1 mg/ml containing 2 mg/ml of Sigma, Type V, bovine serum albumin and 1 mg/ml $CaCl_2$) was injected into the pancreas via the common bile duct. (Gotoh et al., Transplantation 40:437 (1985), Supra). The pancreas was removed and collected in a flask maintained on ice. Once pancreata from 4 rats had been collected, the flask was placed in a waterbath, at 38° C., for 30 minutes. The resulting digested tissue was washed 4 times in cold (8° C.) HBSS (Hank's Balanced Salts Solution).

Undigested tissue, large lymph nodes, and other extraneous material were removed by repeated mobilization of the tissue, followed by removal of the supernatant. Purified islets were isolated on a discontinuous Ficoll gradient, consisting of 25%, 23%, 21%, and 11% Ficoll layers, prepared in Euro-Collins solution (Frescenius A. G., Gluehen Steinweg, Hornburg V. D. H.) and centrifuged at 2000 r.p.m. for 16 minutes. The islets were collected from the interface between 11% and 21% and the interface between 21% and 23% Ficoll layers. Islets from each fraction were pooled and washed four times in HBSS solution containing 10% fetal calf serum.

The pooled islets cells were then transferred to petri dishes containing RPMI complete medium, i.e., cold RPMI 1640 medium (GIBCO, Grand Island, N.Y.), supplemented with 25 mM HEPES, heat-inactivated fetal bovine serum (10%), and antibiotic-antimycotic solution (1 ml/100 ml) which contains: 100 μg/ml of penicillin, 100 μg/ml of streptomycin sulfate, and 25 μg/ml of amphotericin B. Any remaining non-islet acinar, vascular, ductular, or lymph node tissue was identified with the aid of a dissecting microscope, and carefully removed with a fine-tip sterile pipette. Final purity was assessed by staining the islet preparation with diphenylthiocarbazone.

After isolation, the islets were incubated in bacteriological plastic dishes (100 mm) containing 10 ml of RPMI medium, at 37° C., in a humidified atmosphere having 5% $CO_2$, for 4 days. The medium was changed every day, and the islets were then either directly transplanted or macroencapsulated.

Example II

A. Preparation of Agarose Coated, Agarose-Collagen Pancreatic islet Macrobeads 1000 pancreatic islets obtained by the method of Example I were washed four times in RPMI complete medium as described in Example I, less fetal calf serum. The pancreatic islets were then added to a tube containing 50 μl of 1% atelocollagen solution in phosphate buffered saline, to suspend the pancreatic islets. 100 μl of 1% low viscosity agarose (Sigma Type XII) solution, prepared either in RPMI or in MEM (minimal essential medium), maintained at 60° C., was then added to the collagen-pancreatic islet suspension. The contents of the tube were then transferred immediately, as a single large drop; either onto sterilized mineral oil, maintained at room temperature, or onto a Teflon® sheet. After one minute, the drop became a semi-solid macrobead which was then transferred to RPMI antibiotic medium, at 37° C. The macrobeads were washed three times with the same medium to remove all oil. Finally, they were rinsed twice with complete medium (37° C.) and incubated overnight, at 37° C., in a humidified atmosphere having 5% $CO_2$. During this period, the collagen polymerized and the pancreatic islets rested on the collagen fiber.

Figure 1:
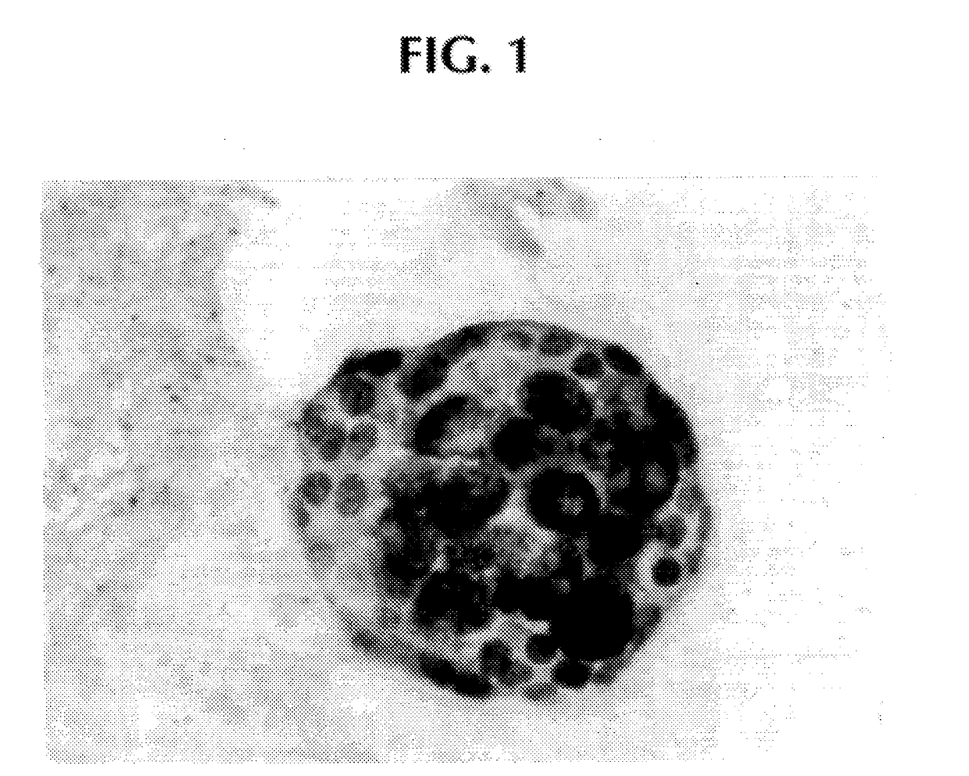
FIGS. 1 and 2 show agarose coated, collagen-agarose pancreatic islet macrobeads.
Figure 2:
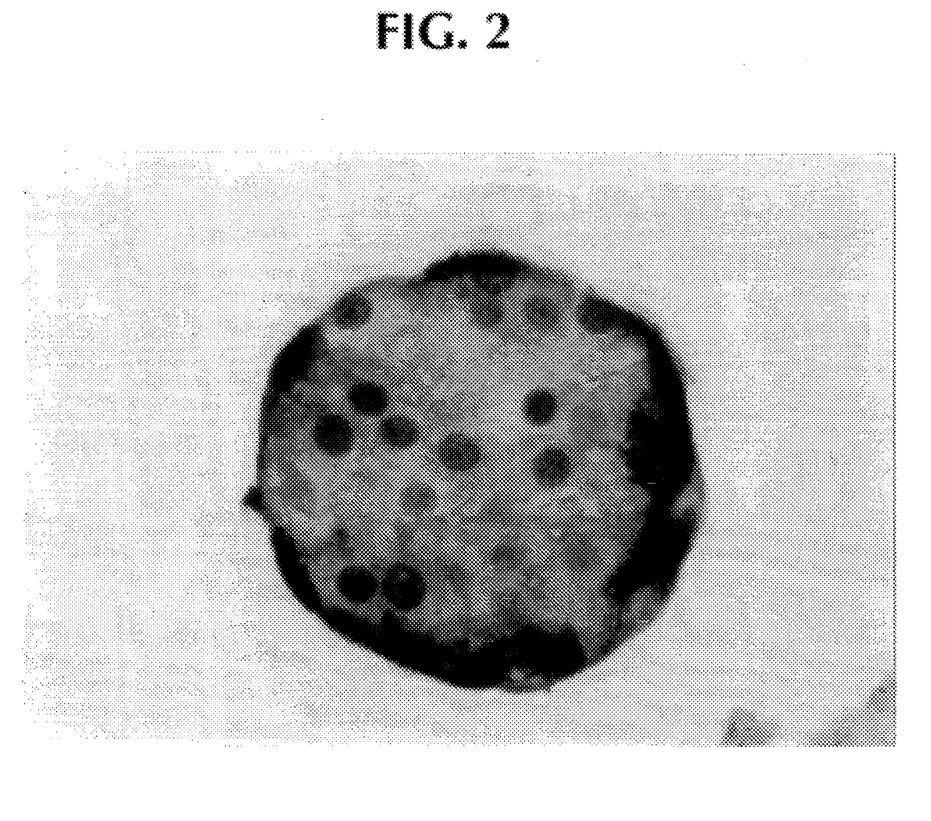

The next day, the solid macrobeads were transferred to a Teflon® spoon which contained approximately 1 ml of 5% agarose in RPMI or in MEM medium. The solid macrobeads were then rolled in this solution 2-3 times in order to uniformly mat them. Before the agarose solidified, the macrobeads were transferred to mineral oil in a Teflon® dish to obtain smooth-surfaced macrobeads. After 60 seconds, the macrobeads were removed from mineral oil and washed 3 times with RPMI antibiotic medium, and then two times with RPMI complete medium. They were then incubated overnight, at 37° C., in a humidified atmosphere having 5% $CO_2$. Agarose coated, agarose-collagen pancreatic islet macrobeads are shown in FIGS. 1 & 2.

B. Preparation of Agarose Coated, Gelatin Sponge Pancreatic Islet Macrobeads

A small piece of gelatin sponge (gelfoam), 3 $mm^2$ was first soaked in RPMI complete medium. The medium was squeezed out and the gelfoam was allowed to rest for 1 minute. One thousand pancreatic islets, prepared according to Example I, were washed four times with RPMI antibiotic medium. They were then suspended in 10 μl of RPMI antibiotic medium. They were transferred by a fine-tipped plastic pipette and spread onto the surface of the gelfoam. After 20 seconds, the gelfoam was rolled into a small sphere. 50 μl of 5% agarose was poured onto the surface of the sphere to create an pancreatic islet macrobead.

In order to uniformly cover the macrobead with 5% agarose, 500 μl of 5% agarose was added to the macrobead in a Teflon® spoon and was rolled 3-4 times. Before the agarose solidified, the macrobead was transferred to mineral oil, and the dish was rotated to obtain a smooth surface on the macrobead. The macrobead was washed 3-4 times in RPMI antibiotic medium and then rinsed 2 times with RPMI complete medium. It was incubated overnight before being used for transplantation.

C. Preparation of Agarose Coated, Agarose Pancreatic Islet Macrobeads

One thousand pancreatic islets obtained by the method of Example I were first washed 4 times in RPMI antibiotic medium. The pancreatic islets were transferred to a tube containing 50 μl RPMI antibiotic medium and suspended thereon. 100 μl of 1% agarose solution was then added to the tube. The entire contents of the tube was immediately transferred, as a single large drop, to either sterilized mineral oil or a teflon sheet. After 1 minute, the drop solidified to a macrobead. The macrobead was transferred to RPMI antibiotic medium, maintained at 37° C. The oil was then removed by washing the macrobead 3 times with the same medium, and then by rinsing 2 times with RPMI complete medium. The beads were incubated overnight at 37° C. in a humidified atmosphere having 5% $CO_2$.

The next day, these beads were transferred onto a Teflon® spoon containing 1 ml of 5% agarose in either RPMI or in MEM medium To uniformly coat the macrobeads with agarose, the beads were then gently rolled in agarose 2-3 times. They were then transferred to mineral oil, in a teflon dish, before the agarose solidified. After 60 seconds, the beads were removed from the mineral oil and washed 3 times in RPMI antibiotic medium and 2 times in RPMI complete medium. The beads were then incubated overnight.

Example III—Transplantation of the Pancreatic Islet Macrobeads Into Mice

A. Recipient Mice & Donor Rats

The mice used were male C57BL/6 and BALB/c stains. Recipient mice were made diabetic by a single i.v. injection of streptozotocin (170–200 mg/kg).

Non-fasting plasma glucose levels were determined before the induction of diabetes. All blood sugar levels in the recipient mice were monitored via tail vein blood samples with an ExacTech Pen Sensor. Only those mice with serum glucose level >400 mg/dl on the day of transplantation were used.

Wistar Furth rats were used as donors for xenotransplantation.

B. Xenotransplantation of Pancreatic islet Macrobeads Into the Peritoneal Cavity At the time of xenotransplantation, pancreatic islet macrobeads of Example II(A), II(B), and II(C), respectively, were transferred gently to separate plates containing RPMI antibiotic medium. To remove all serum proteins, the medium was changed three times. Diabetic recipient mice were anesthetized with avertin. A midline incision was made to introduce a single pancreatic islet macrobead into the free peritoneal cavity. A two-layer closure of the incision was done with an absorbent suture. Control mice received either an empty macrobead i.p. (intrapefitoneally), free pancreatic islets i.p., or an empty macrobead together with free donor pancreatic islets.

After transplantation, each recipient's blood glucose was checked daily or every other day until it reached the normal range; thereafter blood glucose was checked only 2–3 times every week. Transplants were considered technically successful if the serum glucose was <200 mg/dl and remained there for consecutive bleedings. A transplant was considered to have been rejected if the serum glucose concentration rose above 200 mg/dl after a period of transient normoglycemia. Transplants were considered to have failed or to have become 'primary nonfunctional' if the blood glucose never became normal (i.e., consistently remained 200 mg/dl).

C. Intraperitoneal Glucose Tolerance Test

Approximately 70–84 days post-implantation, glucose tolerance tests were performed. Glucose solution (1.0 g/kg body weight) was intraperitoneally injected into mice who had been fasting for 6 hours (9 am–3 pm). Both pre- and post-injection (0, 30, 60,and 120 minutes), blood samples were taken to determine plasma glucose levels using the ExacTech Pen Sensors.

For comparison, glucose tolerance tests were performed on normal C57BL/6 and BALB/c mice, on streptozotocin induced C57BL/6 and BALB/c mice in which no pancreatic islets had been transplanted, and on streptozocin-induced diabetic BALB/c mice in which free pancreatic islets had been transplanted into the kidney capsule ("KCT" mice).

Control experiments were conducted to ensure that the euglycemic state in diabetic mice was being achieved via the macroencapsulated pancreatic islets and not the macrobeads themselves. Empty agarose coated, agarose-collagen macrobeads and agarose coated, gelfoam macrobeads were, therefore, prepared in the same manner as the beads of Examples II(A) and (B).

Figure 3:
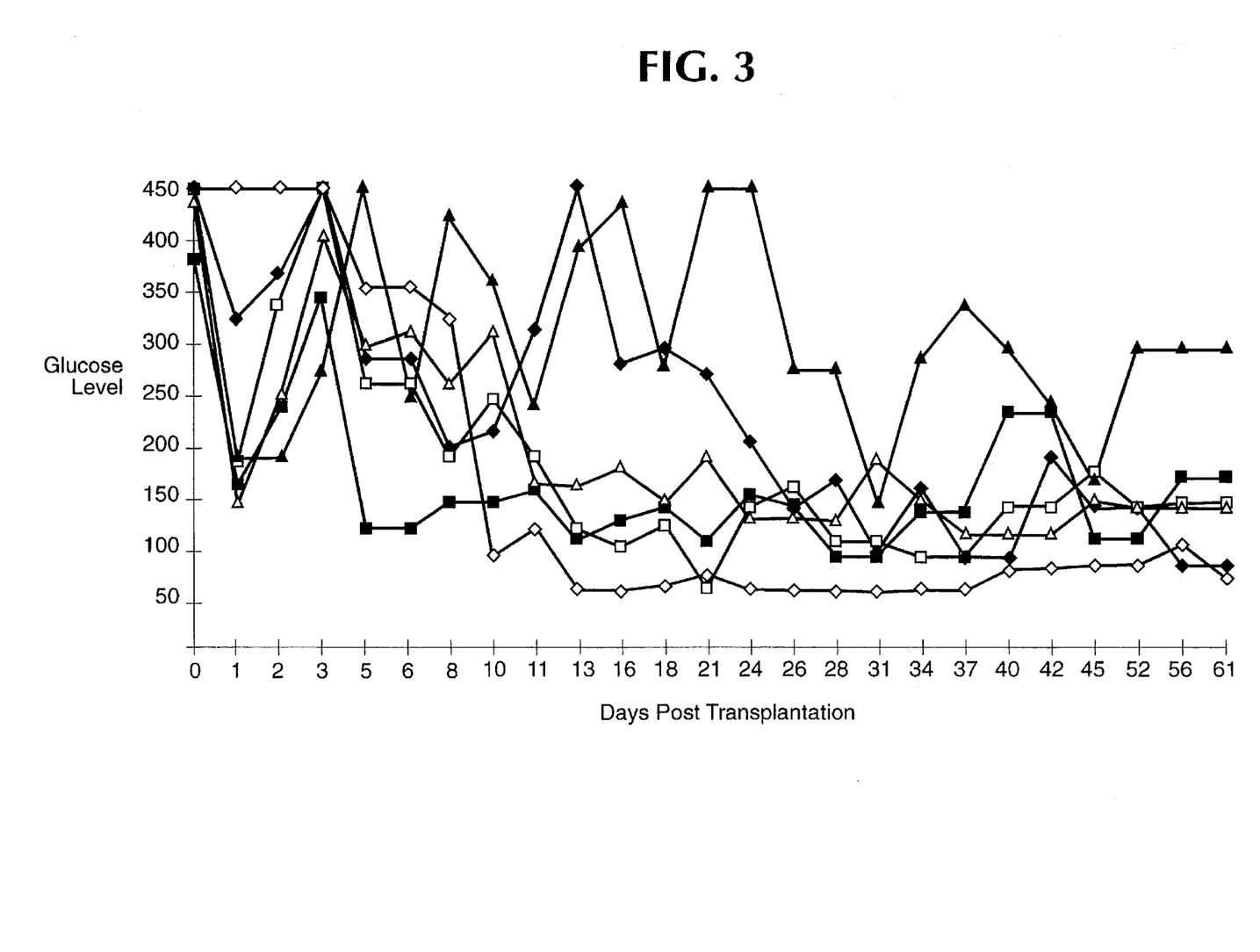
FIG. 3 shows the glucose levels of diabetic mice transplanted with agarose coated, collagen-agarose pancreatic islet macrobeads.
Figure 4:
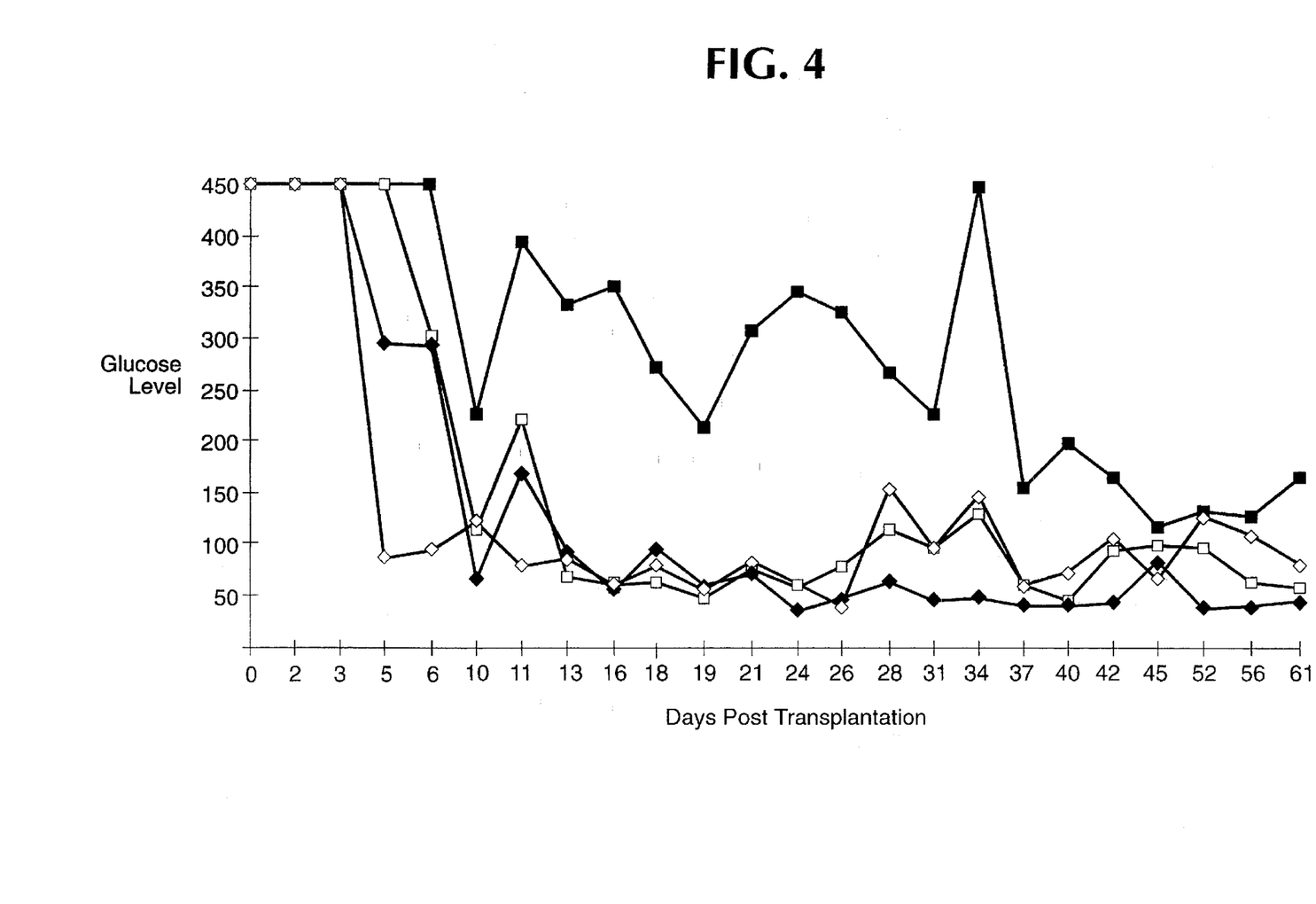
FIG. 4 shows the glucose levels of diabetic mice transplanted with agarose coated, gelfoam pancreatic islet macrobeads.
Figure 5:
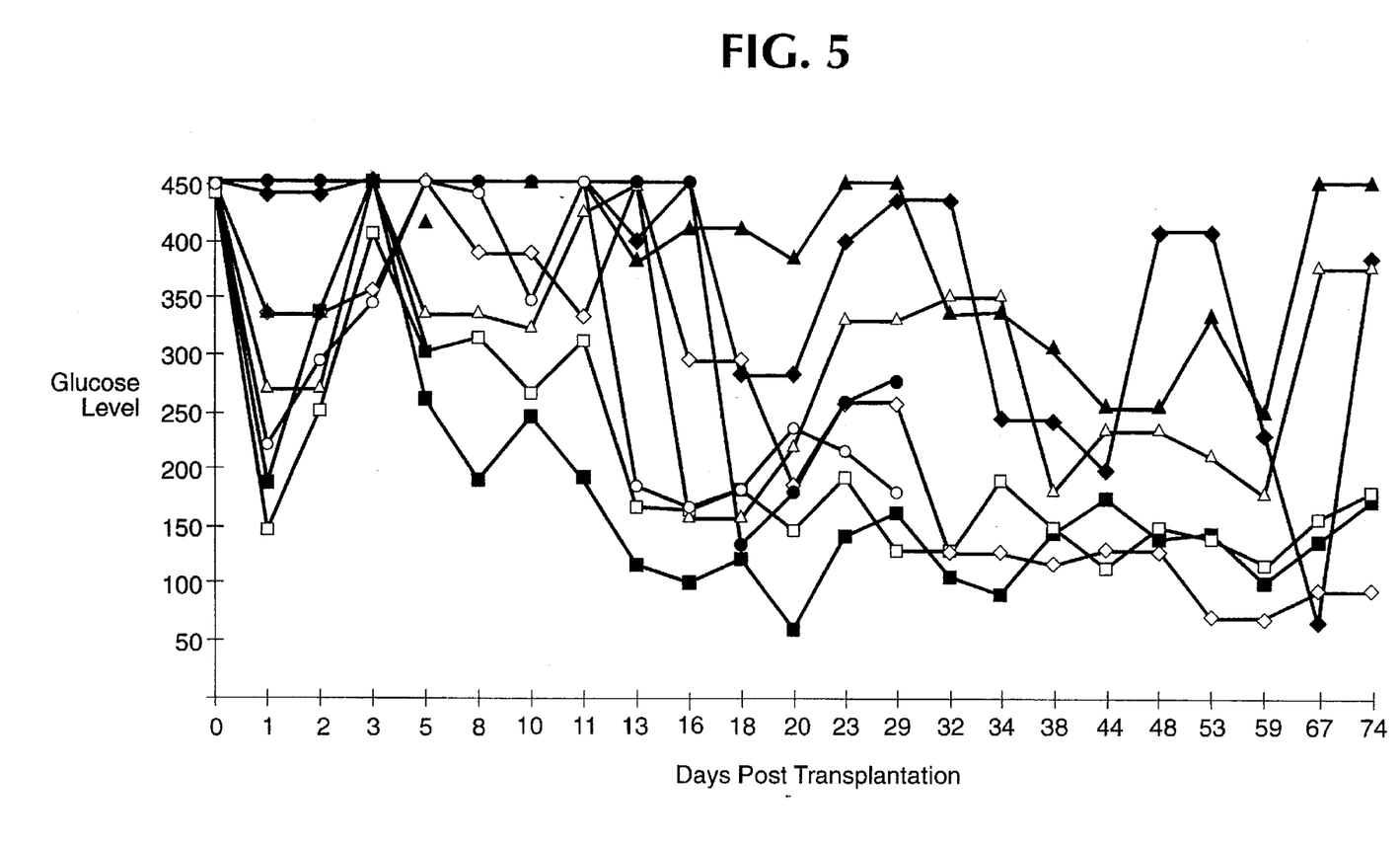
FIG. 5 shows the glucose levels of diabetic mice transplanted with agarose coated, agarose macrobeads.

D. Results of the Intraperitoneal Xenotransplantation and Glucose Tolerance Test Upon implantation of pancreatic islet macrobeads, the changes observed in the non-fasting plasma glucose level of STZ-diabetic streptozotocin induced C57BL/6 mice are shown in FIGS. 3 & 4. The recipients of agarose coated, agarose-collagen pancreatic islet macrobeads and agarose coated, gelfoam pancreatic islet macrobeads maintained a normoglycernic state for more than 60 days and, during this period, the body weight of these mice increased an average of 3 grams. When agarose covered, agarose pancreatic islet macrobeads were transplanted, 2 of 6 animals became normoglycemic after 21–33 days post transplantation (FIG. 5) and remained euglycemic thereafter. All other transplanted animals failed to achieve a euglycemic state. Empty macrobeads (n=6) did not affect blood glucose.

Figure 6:
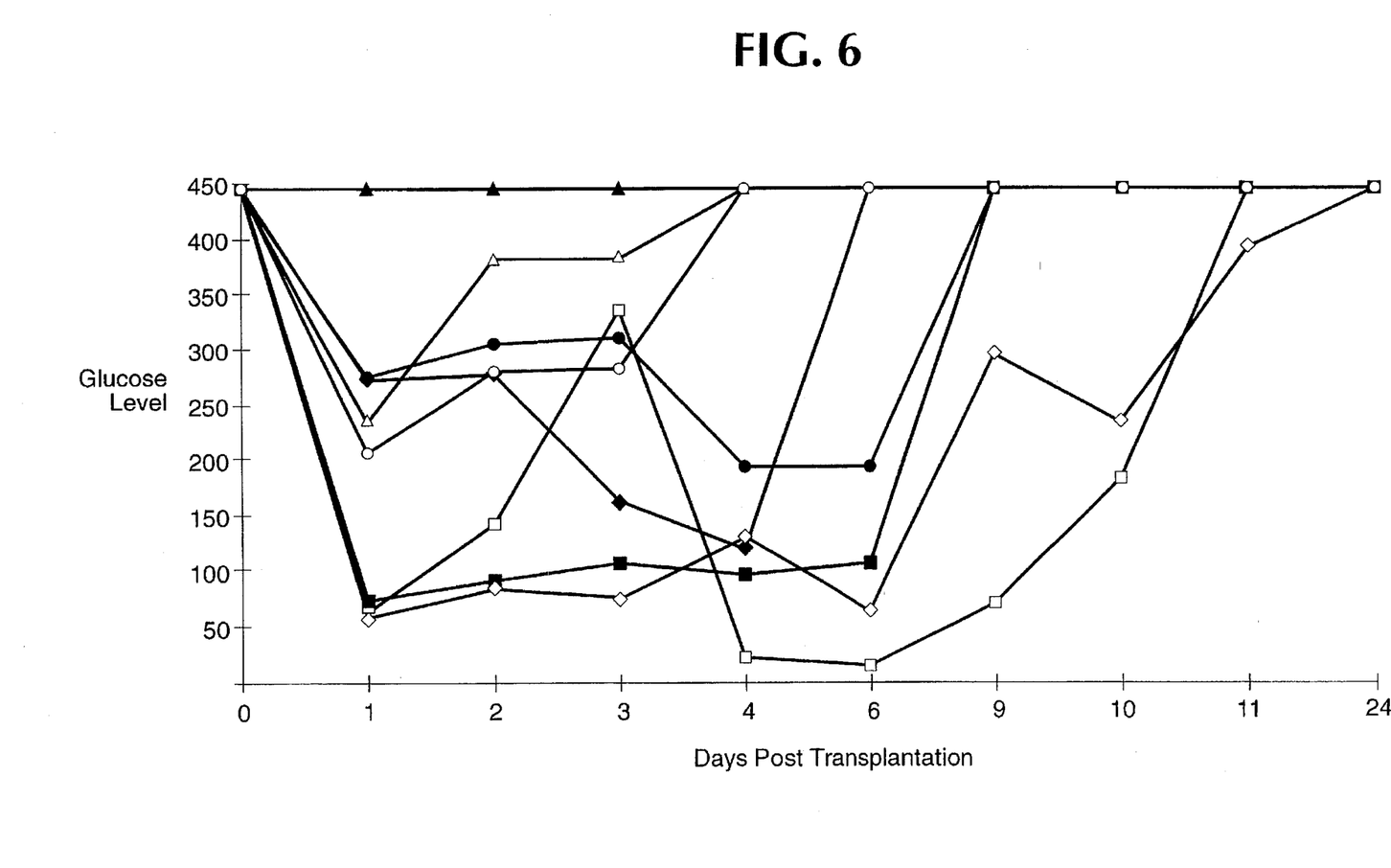
FIG. 6 shows the glucose levels of diabetic mice transplanted with free pancreatic islets.
Figure 7:
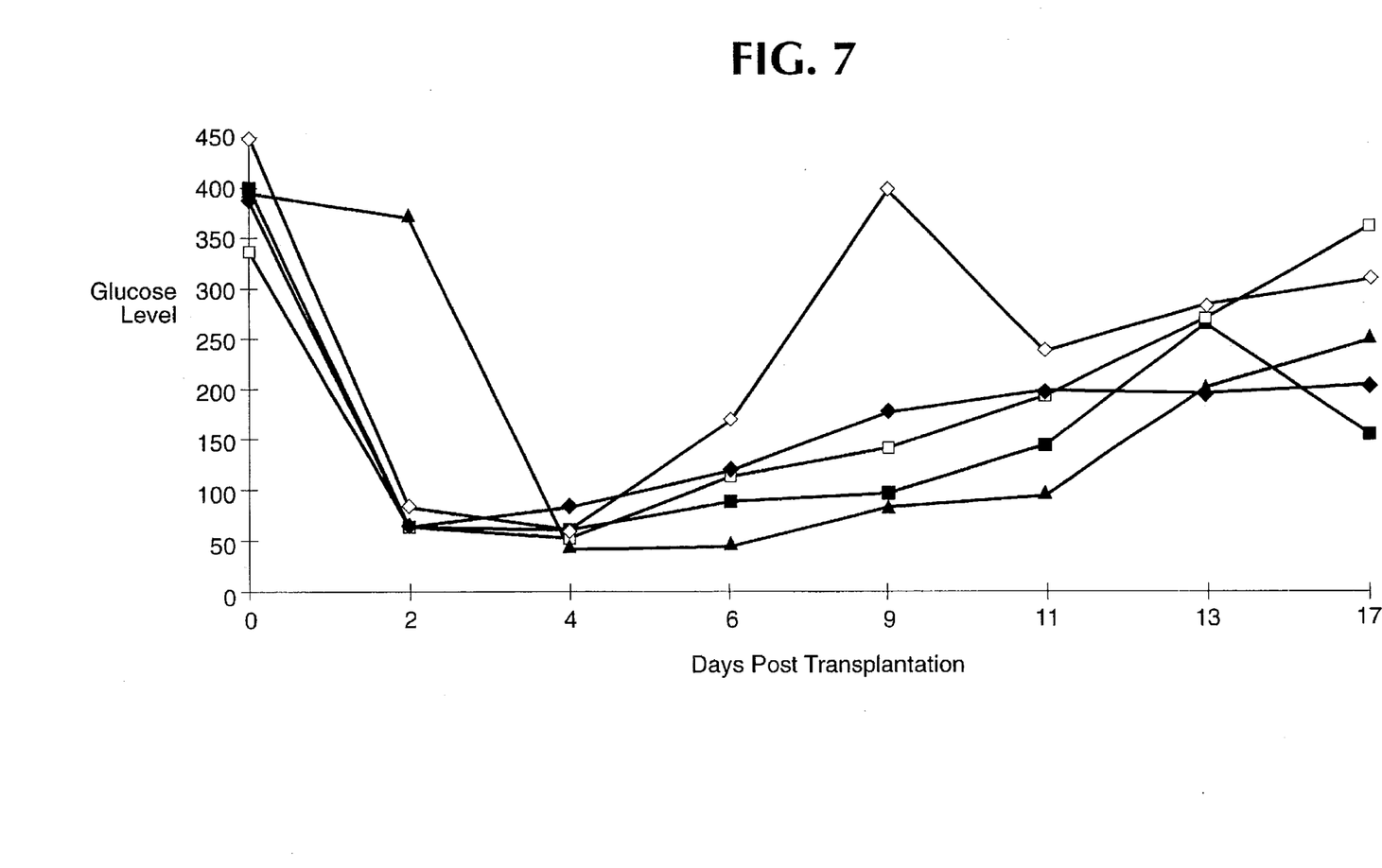
FIG. 7 shows the glucose levels of diabetic mice transplanted with agarose coated, collagen-agarose macrobeads and free pancreatic islets.

When free pancreatic islets were transplanted intraperitoneally, 6 of 7 transplanted animals became normoglycemic 1 day after transplantation; however, they maintained this state for only 3–10 days (FIG. 6). When free pancreatic islets were transplanted with empty beads made of agarose coated, agarose-collagen macrobeads or agaose coated, gelfoam macrobeads, all the animals became normoglycemic within 24 hours and remained so for more than 12 days (FIG. 7). Subsequently, all animals became hyperglycemic. Animals which contained empty macrobeads excited no tissue reaction for the 90 days they were followed.

Figure 8:
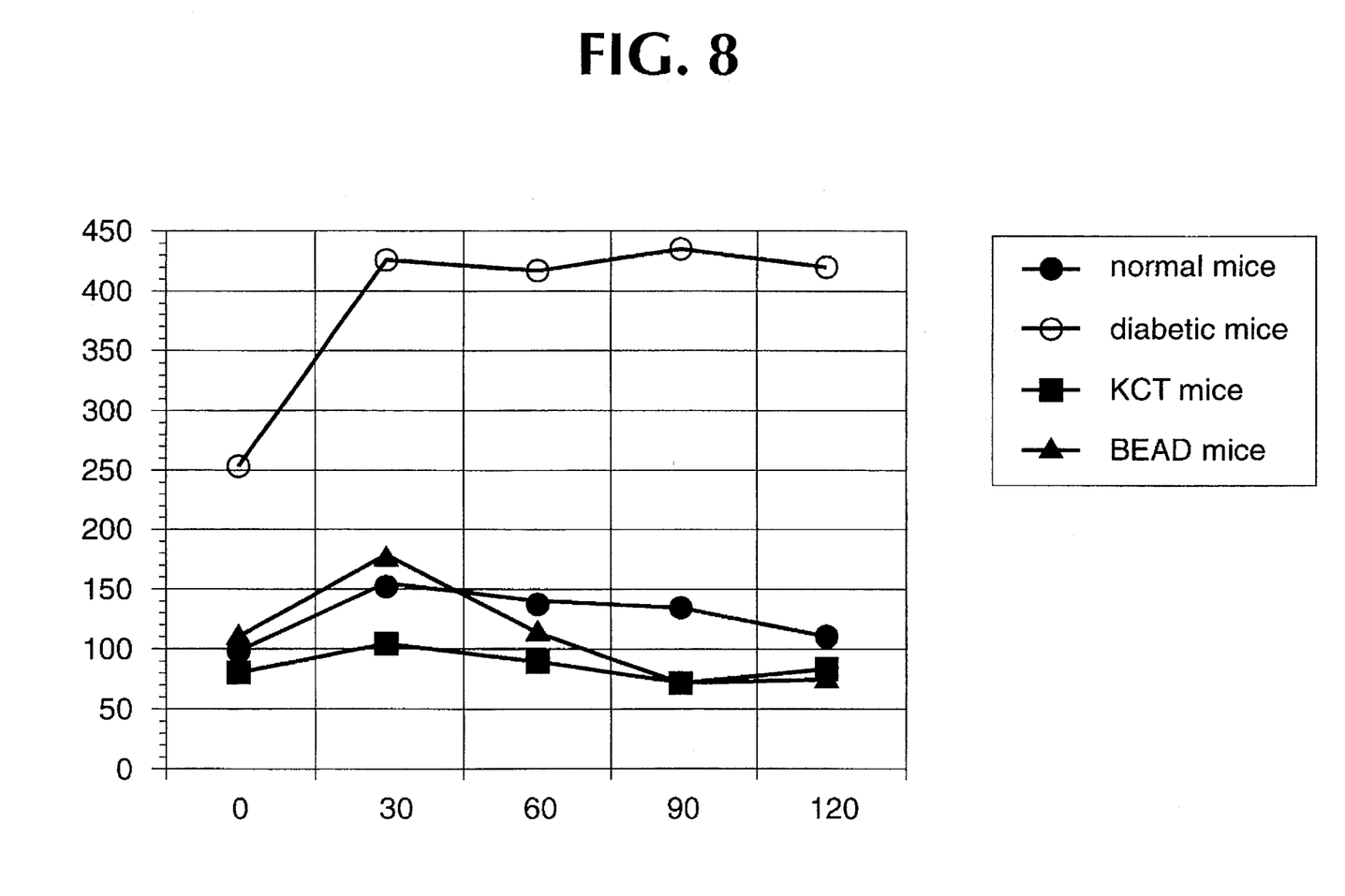
FIG. 8 demonstrates a glucose tolerance test for normal mice, streptozotocin-induced diabetic mice, streptozotocin-induced diabetic mice receiving allotransplant in the kidney capsule "(KCT mice)", and streptozotocin-induced diabetic mice receiving agarose coated, agarose-collagen pancreatic islet macrobeads; agarose coated, gelfoam pancreatic islet macrobeads; and agarose coated, agarose pancreatic islet macrobeads (collectively referred to as "bead mice").

The results obtained after performing the Glucose Tolerance Tests are presented in FIG. 8. In normal BALB/c and C57BL/6 mice and "KCT" mice, plasma glucose peaked at 30 minutes and returned to baseline levels by 120 minutes.

Similar results were obtained when macroencapsulated pancreatic islets and non-encapsulated pancreatic islets transplanted in the kidney capsule were tested.

The results of these experiments demonstrate that the agarose coated, agarose-collagen islet macrobeads; agarose coated, agarose-gelfoam pancreatic islet macrobeads; and agarose coated, agarose islet macrobeads display the properties required for a hybrid artificial organ. Although all three types successfully secrete insulin, agarose coated, agarose-collagen and agarose coated, agarose-gelfoam macrobeads are more suitable as biohybrid artificial organs due to the uniformity of results obtained in the minimum number of transplanted animals. Moreover, all the three types of beads showed no adverse effects. The macrobeads remained free in the peritoneum showing neither tissue reaction, nor any adhesion to any organ. Thus, these biohybrid pancreatic islets perform their function as efficiently in the macroencapsulated beads as in their natural habitat, the pancreas.

In all of the mice, plasma glucose peaked at 30 minutes and returned to baseline levels by 120 minutes.

Example IV

Extended Storage Life of Pancreatic islets

Macroencapsulated beads prepared according to Examples I(A), (B), and (C), which were incubated for 4 weeks at 37C in complete RPMI medium, were tested for their long-term preservation properties in vivo and in vitro. It was found that the macroencapsulated pancreatic islets which were incubated for 4 weeks were functionally similar to those which were incubated for 1 day.

This example demonstrates that the method of macroencapsulation according to the present invention can be used for secretory cell preservation, and preferably, pancreatic islet preservation.

What is claimed is:

1. A method for preparing an agarose coated, solid agarose-collagen bead which contains secretory cells, comprising:

(a) suspending secretory cells in a collagen containing solution, (b) adding agarose to said solution, (c) forming a semi-solid bead of said collagen, agarose, and secretory cells, (d) polymerizing collagen in said semisolid bead to form a solid, agarose-collagen bead containing secretory cells, and (e) coating said solid, agarose-collagen bead containing secretory cells with agarose.

2. The method of claim 1, wherein said secretory cells are contained in pancreatic islets.

3. The method of claim 2, wherein said pancreatic islets are human pancreatic islets, bovine pancreatic islets, rat pancreatic islets or porcine pancreatic islets.

4. The method of claim 3, wherein said pancreatic islets are human pancreatic islets.

5. The method of claim 1, wherein said secretory cells are contained in from about 50,000 to about 700,000 pancreatic islets.

6. An agarose coated, solid agarose-collagen bead containing secretory cells prepared by the process of claim 1.

7. The agarose coated, solid agarose-collagen bead of claim 6, wherein said secretory cells are contained in pancreatic islets.

8. The agarose coated, solid agarose-collagen bead of claim 6 wherein said pancreatic islets are human pancreatic islets, bovine pancreatic islets, rat pancreatic islets or porcine pancreatic islets.

9. The agarose coated, solid agarose-collagen bead of claim 8, wherein said pancreatic islets are human pancreatic islets.

10. The agarose coated, solid agarose collagen bead of claim 7, comprising from about 50,000 to about 700,000 islets.

11. Method for treating a mammal having a condition caused by impaired secretory cell function, comprising:

transplanting into said mammal a therapeutically effective amount of the agarose coated, solid agarose-collagen bead of claim 6.

12. The method of claim 11, wherein said condition is insulin dependent diabetes.

13. The method of claim 12, wherein said bead contains cells derived from a pancreatic islet.

14. The method of claim 13, wherein said pancreatic islet is a human pancreatic islet.

15. The method of claim 13, wherein said pancreatic islet is a bovine pancreatic islet.

16. The method of claim 13, wherein said pancreatic islet is a porcine pancreatic islet.

17. The method of claim 11, wherein said bead is placed in the peritoneal cavity of said mammal.

* * * * *